United States Patent
Agee et al.

(10) Patent No.: US 9,861,409 B1
(45) Date of Patent: Jan. 9, 2018

(54) METHOD AND APPARATUS FOR FRACTURE REDUCTION DURING INTERNAL FIXATION OF DISTAL RADIUS FRACTURES

(71) Applicant: JOHN M. AGEE, TRUSTEE OF THE JOHN M. AGEE TRUST OF AUG. 15, 1996, Sacramento, CA (US)

(72) Inventors: John M. Agee, Cameron Park, CA (US); Jeffrey Woodhouse, Sacramento, CA (US); Francis C. King, Sacramento, CA (US)

(73) Assignee: John M. Agee, Sacramento, CA (US), TRUSTEE OF THE JOHN M. AGEE TRUST OF AUG. 15, 1996

( * ) Notice: Subject to any disclaimer, the term of this patent is extended or adjusted under 35 U.S.C. 154(b) by 662 days.

(21) Appl. No.: 14/495,572

(22) Filed: Sep. 24, 2014

Related U.S. Application Data

(60) Provisional application No. 61/881,787, filed on Sep. 24, 2013.

(51) Int. Cl.
| | |
|---|---|
| *A61B 17/56* | (2006.01) |
| *A61B 17/84* | (2006.01) |
| *A61B 17/88* | (2006.01) |
| *A61B 17/68* | (2006.01) |
| *A61B 17/80* | (2006.01) |

(52) U.S. Cl.
CPC ........ *A61B 17/846* (2013.01); *A61B 17/8872* (2013.01); *A61B 17/8897* (2013.01); *A61B 17/808* (2013.01); *A61B 17/8061* (2013.01); *A61B 2017/564* (2013.01); *A61B 2017/681* (2013.01)

(58) Field of Classification Search
CPC . A61B 17/66; A61B 17/6425; A61B 17/6466; A61B 17/68
USPC .......... 606/54–59, 60, 250–278, 329, 96–98, 606/104–105; 81/484, 177.1
See application file for complete search history.

(56) References Cited

U.S. PATENT DOCUMENTS

| | | | | |
|---|---|---|---|---|
| 2,002,021 A | * | 5/1935 | Rouse ................ | A61B 17/6408 606/105 |
| 3,386,437 A | * | 6/1968 | Treace ............... | A61B 17/8019 254/126 |
| 3,709,219 A | * | 1/1973 | Halloran ................ | A61B 17/66 606/105 |
| 4,383,527 A | * | 5/1983 | Asnis ................ | A61B 17/1721 606/96 |
| 4,628,922 A | * | 12/1986 | Dewar ................... | A61B 17/66 606/54 |
| 5,846,245 A | * | 12/1998 | McCarthy ............ | A61B 17/663 606/105 |

(Continued)

*Primary Examiner* — Tatiana Nobrega
*Assistant Examiner* — Jessica Weiss
(74) *Attorney, Agent, or Firm* — O'Banion & Ritchey LLP; John P. O'Banion

(57) ABSTRACT

An apparatus for treating a fracture of the distal radius of a patient, having a pivot pin configured to engage the radius at an attachment point distal to the fracture, and a handle assembly configured to engage the pivot pin dorsal to the patient's hand is presented. The pivot pin is configured to insert through and fixedly engage at least a portion of the distal fracture bone fragment associated with the radius. The handle assembly, once coupled to the pivot pin, provides adjustment of the position of the distal fracture bone fragment.

12 Claims, 5 Drawing Sheets

(56) References Cited

U.S. PATENT DOCUMENTS

| | | | | |
|---|---|---|---|---|
| 7,008,432 B2 * | 3/2006 | Schlapfer | ............. | A61B 17/025 606/105 |
| 2009/0048598 A1 * | 2/2009 | Ritchey | ............. | A61B 17/1725 606/57 |
| 2012/0253410 A1 * | 10/2012 | Taylor | ................ | A61B 17/6458 606/329 |

* cited by examiner

METHOD AND APPARATUS FOR FRACTURE REDUCTION DURING INTERNAL FIXATION OF DISTAL RADIUS FRACTURES

CROSS-REFERENCE TO RELATED APPLICATIONS

This application claims priority to, and the benefit of, U.S. provisional patent application Ser. No. 61/881,787 filed on Sep. 24, 2013, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technical Field

This description pertains generally to treatment of fractures of the distal radius, and more particularly to reduction and stabilization of distal radius fractures during installation of an internal fixation plate.

2. Description of Related Art

Fractures of the distal radius, often called Colles' fractures, are a common injury among adults. The fracture typically occurs when one begins to fall and extends one's hand as a reflex to lessen the force of hitting the ground. The fall produces a sudden impact of the body weight on the heel of the hand, which results in a dorsally displaced fracture of the radius just proximal to the wrist joint with or without an associated wrist joint injury.

Reduction of the crushed and displaced bones toward normal alignment is typically performed by the surgeon using manual manipulation. Once optimum alignment is achieved through manual manipulation, an internal fixation device, often called a volar plate, is applied. These devices generally include a metal plate that is inserted through an incision on the palmar side of the forearm. The plate spans the fracture site by securing to both the intact portion of the shaft of the radius bone and the fractured distal fragments using various screw, pin, and peg arrangements. Internal fixation plates are designed to stabilize the fracture fragments and injured soft tissue as they heal. However, these fixation plates do not provide either the initial alignment or stabilization of the fracture fragments that are required during surgery for installation of a fixation plate.

Initial alignment of the bone fragments (fracture reduction) is a complex task in view of the numerous degrees of freedom in the region of the forearm, wrist and hand. The typical fracture causes misalignment of the distal fragments both rotationally and translationally with respect to a conventional set of orthogonal anatomical axes of the forearm, wrist and hand. Translational misalignment can occur for example in the radial-ulnar, palmar-dorsal, and proximal-distal directions. Rotational misalignment can occur about the longitudinal axis of the radius, or other axes. All of these misalignments must be considered and addressed for restoring the anatomy as close to normal as possible before attachment of the fixation plate. Currently, surgeons use both finger traction devices and various manual manipulations of the patient's wrist and hand to achieve an optimal fracture reduction. These maneuvers typically include distal distraction of the hand to restore length to the radius, ulnar deviation, and wrist flexion to restore the tilt of the distal radial articular surface as close as possible to normal.

Once the manipulations have obtained the best realignment of the fracture anatomy, the surgeon must stabilize the reduced fracture fragments while fluoroscopy is used to confirm that correct alignment of the bone fragments has been achieved. In order to stabilize the reduced fracture, the surgeon typically must either manually try to hold the fracture stable or use various pinning techniques (e.g. K-wires that pass through holes in the volar plate and into the fractured radius to stabilize the fracture's alignment). If the fracture fragments are not adequately aligned, further manipulation is performed, followed by additional fluoroscopic imaging.

The process of manipulating the fracture followed by obtaining multiple fluoroscopic images results in two disadvantages for the surgeon. First, stabilizing the fracture reduction can be time consuming and requires either the use of both of the surgeon's hands or an assistant. Consequently, the surgeon may be unable to simultaneously attend to other issues that may require use of his hands.

Second, because the fracture reduction is achieved only when the surgeon is holding the patient's wrist and hand, the surgeon is exposed to radiation from the fluoroscopy each time it is used to image the status of the fracture reduction.

Therefore, a method and apparatus that would facilitate both optimal fracture reduction and maintenance of the reduction during internal fixation would offer improvements over the current surgical methods.

SUMMARY

According to an aspect of the disclosure, an apparatus and method is provided for both reducing the displaced fragments of a fracture of the distal radius toward normal anatomical alignment and holding the fracture reduced during the surgeon's application of suitable internal fixation, such as one of the now well accepted volar plate devices, to the fracture.

In one embodiment, the fracture reduction apparatus comprises a pivot pin that inserts through a hole in a volar plate, traverses through the distal fracture fragment of the radius, and exits the patient's hand dorsally through the extensor retinaculum; and a handle assembly that attaches to the dorsal end of the pivot pin.

In another embodiment, during a surgery for reduction and internal fixation of a fracture of the distal radius using a volar plate, a standard surgical exposure on the palmar side of the patient's distal forearm is used for both accessing the fracture and installing the volar plate. The pivot pin of the present disclosure provides an interface with the distal fracture fragment of the radius for attachment of the handle assembly. To install the pivot pin, the volar plate is first positioned against the radius at the approximate location where it will be attached. At this location, a pivot pin is drilled from palmar to dorsal, through one of the holes in the volar plate, into a distal fragment of the radius. In one embodiment, the pivot pin comprises a k-wire with a spherical stop on one end and a sharpened bone-cutting tip on the opposite end. The sharpened tip enables drilling of the pivot pin through the bone as it is rotated using a standard surgical power drill. The spherical stop provides an interface with a hole in the volar plate to prevent the pivot pin from passing through the volar plate, thereby providing a pivotal interface surface between the spherical stop and countersunk hole in the volar plate. Once inserted, the pivot pin passes through a hole in the volar plate, the distal fragment of the radius, the extensor retinaculum, and exits the dorsal surface of the patient's hand, with the sharpened tip end of the pivot pin exposed.

The handle assembly provides the dorsal interface with the pivot pin. In one embodiment, the handle assembly is composed of a T-handle with a dorsal platform and pivot link. Holes in the dorsal platform and pivot link enable them to be slidably received onto the pivot pin. By sliding the handle assembly from dorsal to palmar on the pivot pin, the dorsal platform contacts the dorsal surface of the patient's hand. While holding the dorsal platform in place against the dorsal surface of the patient's distal forearm (at and distal to the fracture site), the pivot pin is then pulled in a dorsal direction to engage the spherical stop on the pivot pin with the hole in the volar plate. The pivot pin then is secured to the pivot link using a setscrew. The proximal end of the T-handle is slidably attached to the pivot link and is free to rotate about the longitudinal axis of the pivot link. With the surgeon's hand gripping the distal end of the T-handle, a force is applied to the pivot pin.

To achieve alignment and stabilization of the fracture fragments of the distal radius, the surgeon uses his hand to apply forces to the T-handle in a sequenced series of directions. First, the surgeon applies a force to the T-handle in a distal direction to achieve distraction of the fracture fragments, aligning the fragments in the proximal-distal direction. Second, the surgeon applies a force to the T-handle in a palmar direction to achieve palmar tilt of the fracture fragments. Additional translational or rotational forces may be applied by the surgeon to the T-handle to achieve optimum alignment of the fracture fragments with the distal end of the shaft of the radius. The combination of these force applications combined with the attachment location of the pivot pin traversing through both the distal fracture fragment and the extensor retinaculum are sufficient to restore length, appositional alignment, palmar tilt, and ulnar inclination to the fractured radius.

The inventive methods and apparatuses provide for both reduction and stabilization of a displaced fracture of the distal radius during surgical installation of a volar plate. This provides several advantages over prior techniques, including (a) minimizing radiation exposure to the surgeon's hands during fluoroscopy of the fracture; (b) optimal fracture reduction by interfacing directly with the fracture fragments and extensor retinaculum that lies directly adjacent to the fracture fragments; (c) stabilization of the fracture as the position of the patient's forearm and hand are moved for either fluoroscopic imaging or better viewing by the surgeon; (d) adjustment features that provide movements of the fracture fragments in easily understood directions, proximal-distal and palmar-dorsal; and (e) reduced surgical time.

Further aspects of the disclosure will be brought out in the following portions of the specification, wherein the detailed description is for the purpose of fully disclosing preferred embodiments of the disclosure without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
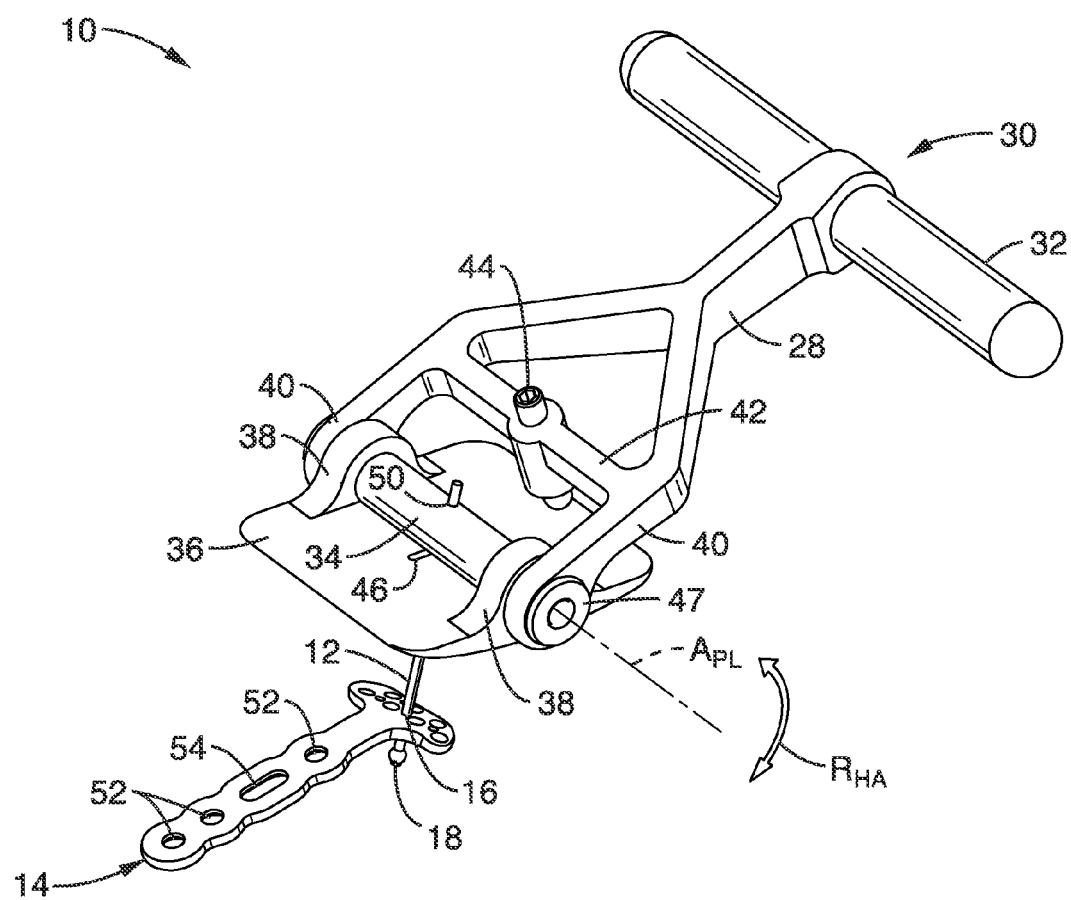
FIG. 1 is a perspective view diagram of a first embodiment of a fracture reduction apparatus of the present disclosure.
Figure 2:
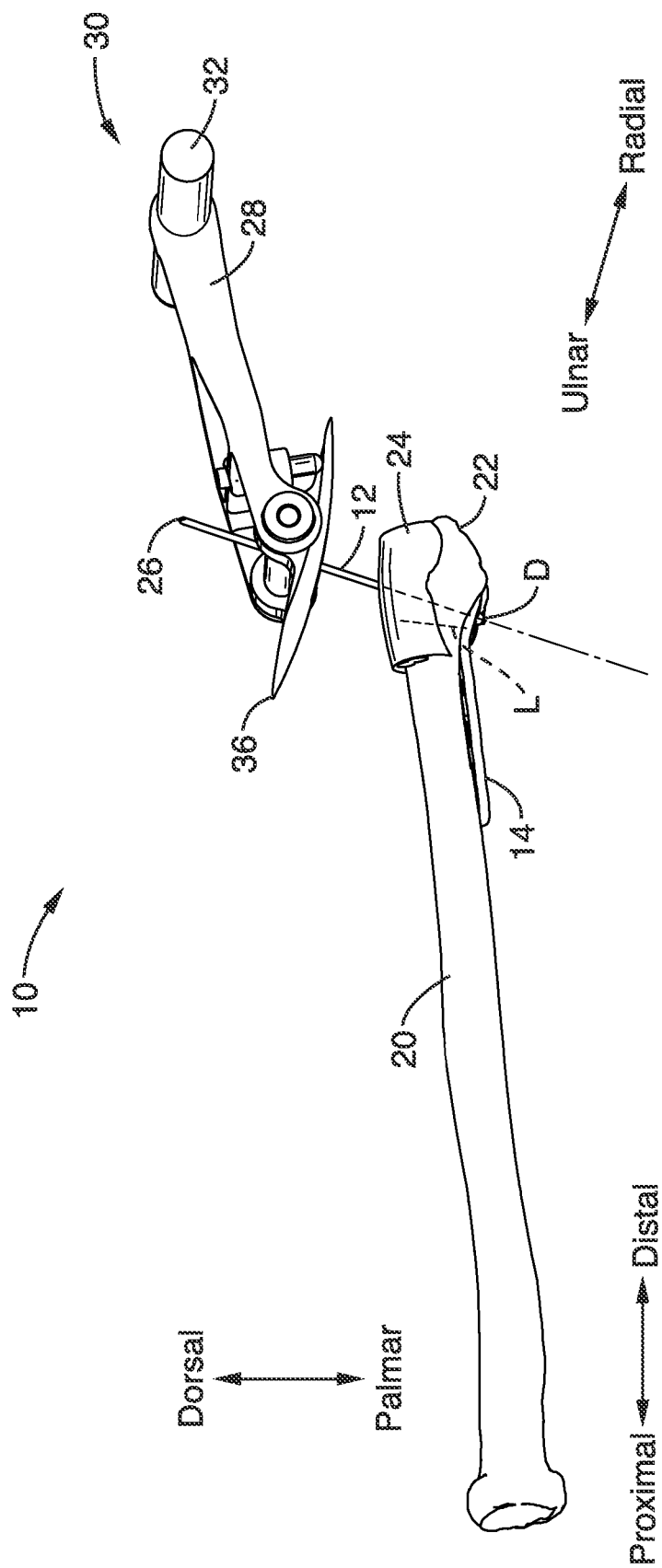
FIG. 2 is a perspective view diagram of the apparatus of FIG. 1 engaged with the radius of a patient.
Figure 4:
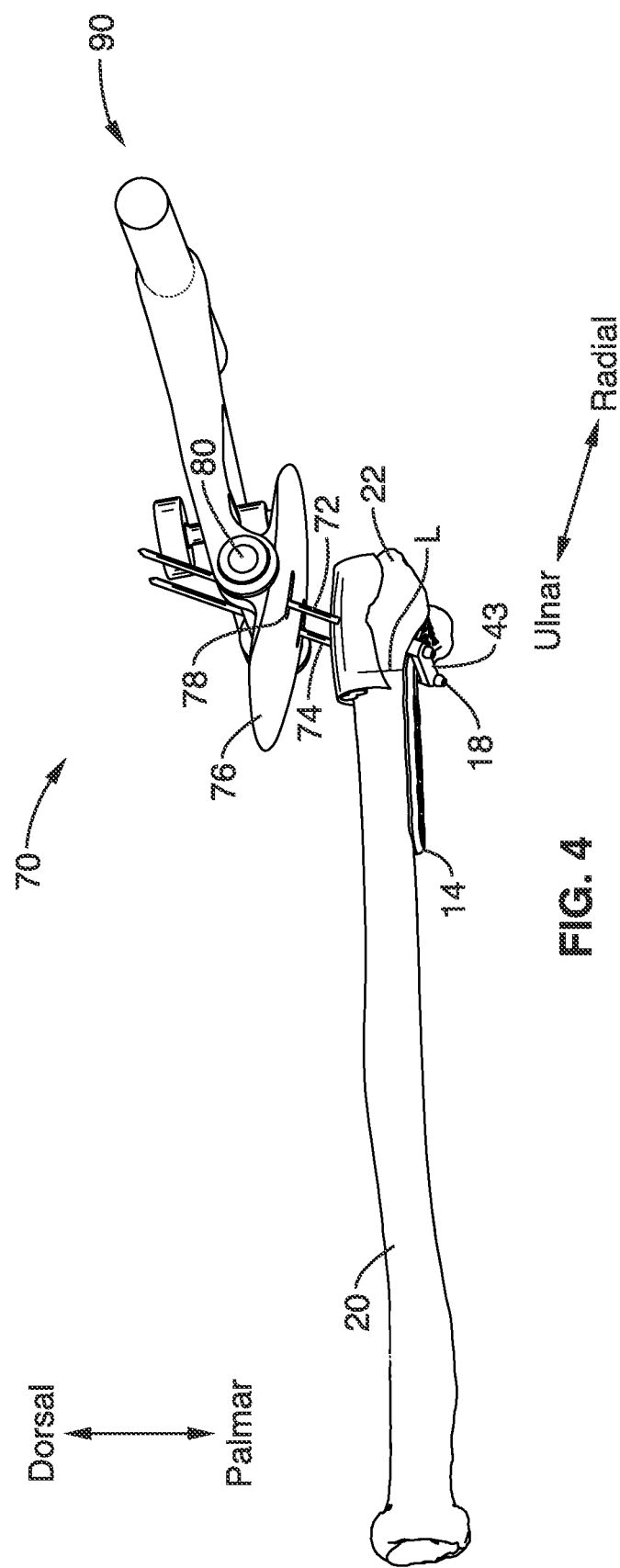
FIG. 4 is a perspective view diagram of an alternative embodiment of the fracture reduction apparatus of FIG. 2 having two pivot pins in accordance with the present disclosure.

FIG. 1 and FIG. 2 show a first embodiment of a fracture reduction apparatus 10 according to the disclosure, for reducing and stabilizing a fracture at the distal end of a radius 20 prior to and during surgical installation of a volar plate 14. For purposes of clarity, only the radius 20 and extensor retinaculum 24 are shown in FIG. 2 and FIG. 4. All other anatomy, including other bones and tissues (e.g. ligaments, tendons, musculature, skin, etc.), are excluded from these illustrations.

Figure 5:
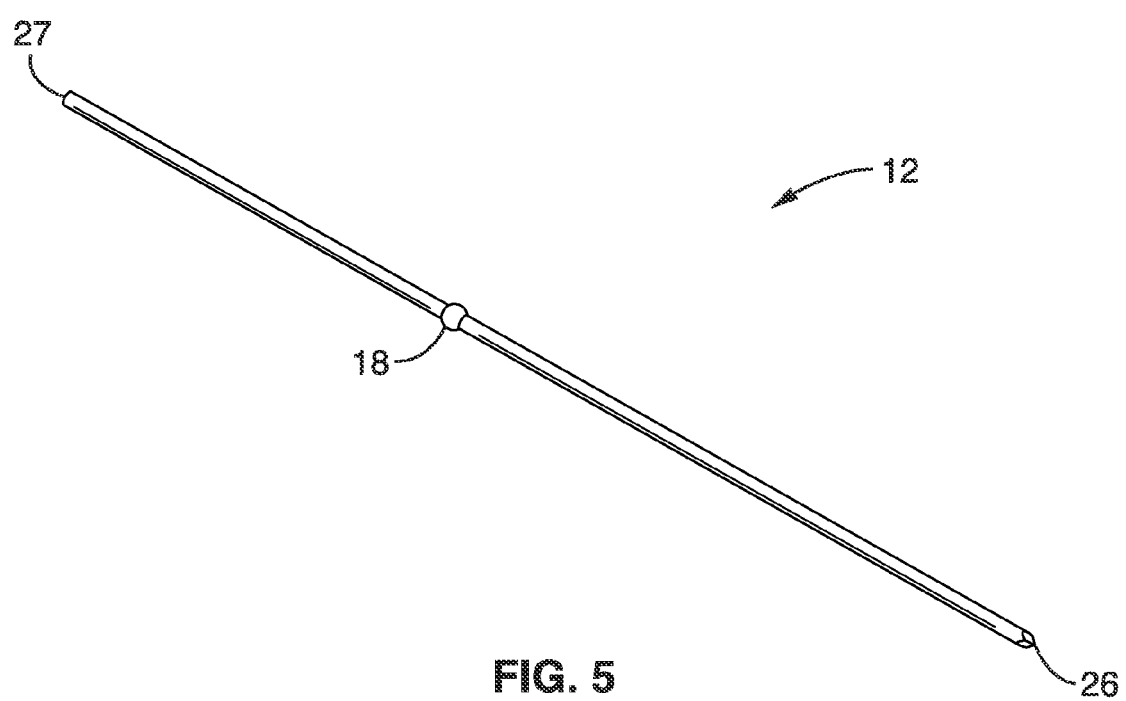
FIG. 5 is a perspective view diagram of a pivot pin used in the apparatus of FIG. 1 through FIG. 4.

In the embodiment shown in FIG. 1 and FIG. 2, the fracture reduction apparatus 10 comprises a pivot pin 12 (shown in further detail in FIG. 5) for creating an attachment point at a distal location D at a point distal to a distal fracture line L, and that inserts through a hole 16 in the volar plate 14.

Apparatus 10 further comprises a handle assembly 30 comprising a pivot link 34 for slidably coupling a T-handle 32 and a dorsal platform 36 with the pivot pin 12 (both prior to and during reduction).

In a preferred method of the present disclosure, the surgeon exposes the fracture of the radius 20 (e.g. using a standard surgical incision), and positions the volar plate 14 against the volar (palmar) surface of radius 20 at the approximate location required to stabilize the distal fracture fragment(s) 22 (see FIG. 2 and FIG. 3A through FIG. 3C). Once the approximate position of the volar plate 14 is established, the surgeon selects one of the holes 16 in the distal end of the volar plate 14 to use for insertion of the pivot pin 12 (shown in uncut form in FIG. 5).

At the location D shown in detail in FIG. 2 (i.e., the distal attachment point as determined by the surgeon), the surgeon inserts sharpened tip 26 of the pivot pin 12 from palmar to dorsal into the distal fracture fragment or fragments 22 using the opposing end 27 of the pivot pin 12, with the sharpened tip 26 generating the path through the bone. The sharpened end 26 of the pivot pin 12 exits through the extensor retinaculum 24 and the skin of the dorsal surface of the distal forearm (not shown), adjacent the patient's fracture. Toward the opposite end 27 (see FIG. 5) of the pivot pin 12, a spherical stop 18 is provided that is configured to both prevent the pivot pin 12 from passing through the hole 16 in the volar plate 14 (spherical stop 18 has a diameter larger than the thru-hole 16 in the volar plate 14) and provides a pivotal interface with the countersunk surface (not shown) of the hole 16 in the volar plate 14.

The exposed dorsal extent of sharpened end 26 of the pivot pin 12 provides an interface with the handle assembly 30. The handle assembly 30 includes a dorsal platform 36 with a slot 46 that extends in a proximal-to-distal direction through the dorsal platform 36. The slot 46 permits translational movement of the dorsal platform 36 in a proximal-distal direction when the pivot pin 12 is inserted through the slot 46.

Located on the dorsal surface of the dorsal platform 36 are two bearing blocks 38, each located adjacent to and on opposite sides of the slot 46, with one offset in the radial direction and the other offset in the ulnar direction. Each bearing block 38 has a hole that provides for slidable insertion of the pivot link 34.

The handle assembly 30 further comprises an arm 28 coupled to T-handle 32 that bifurcates on its proximal end into radial and ulnar link connectors 40. At the proximal ends of each link connector 40 are holes that align with the holes in each corresponding bearing block 38. A pivot link 34 is slidably attached to connect the radial link connector 40 and radial bearing block 38 with the ulnar link connector 40 and ulnar bearing block 38. An aperture or pin hole 50 located midway between the two ends of the pivot link 34 traverses through the pivot link 34 perpendicular to its longitudinal axis $A_{PL}$. Distal to each end of the radial and ulnar link connectors 40 is a crosslink connector 42 that joins between the radial and ulnar link connectors 40 and supports an adjustment screw 44.

The handle assembly 30 is attached to the exposed dorsal end of the pivot pin 12 by sliding the pivot pin 12 through both the slot 46 in the dorsal platform 36 and the pin hole 50 in the pivot link 34.

Figure 3A:
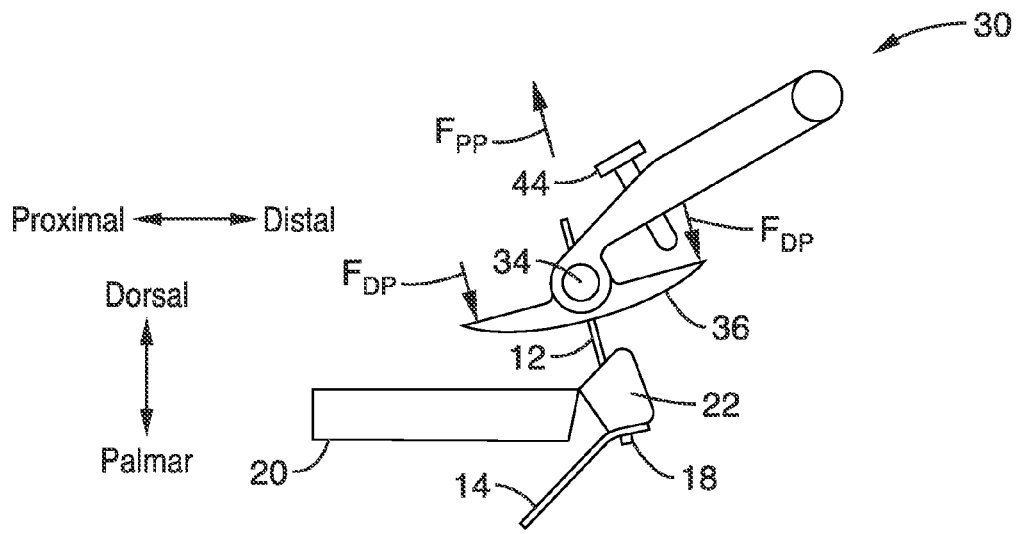
FIG. 3A through FIG. 3C are perspective view diagrams showing assembly of the fracture reduction apparatus and the force applications used to align the fracture fragments.

FIG. 3A shows the handle assembly 30 being inserted onto the pivot pin 12 with the surgeon applying simultaneous forces to both the dorsal platform 36 in the palmar direction $F_{DP}$ and the pivot pin 12 in the dorsal direction $F_{PP}$. With the dorsal platform 36 resting on the dorsal surface of the patient's distal forearm, overlying the fracture, and the spherical stop 18 snug against the hole 16 in the volar plate 14, the handle assembly 30 is secured to the pivot pin 12 by tightening a lock screw 47 (FIG. 1), which extends along the longitudinal axis $A_{PL}$ of the pivot link 34. Lock screw 47 secures the pivot pin 12 to the pivot link 34, while still allowing rotation $R_{HA}$ of the handle assembly 30 about the longitudinal axis $A_{PL}$ of the pivot link 34. In a preferred embodiment, lock screw 47 (see FIG. 1) comprises a set screw, or the like fastener, which may be rotated inward within a central channel (not shown) of the pivot link 34 to impinge on and form a frictional fixation with pivot pin 12. Internal threads (not shown) may be provided in the corresponding bearing block 38 or pivot link 34 for advancement of the lock screw 47.

Once secured, the exposed portion of the sharpened end 26 of the pivot pin 12 may then be cut, as shown in the cut configuration of FIG. 1. The opposite end 27 may also be cut down to the stop 18 (also shown in FIG. 1). The pivot pin 12 may be cut by the surgeon with wire cutters or the like device.

With the handle assembly 30 secured to the pivot pin 12, the surgeon uses one of his hands to grip the T-handle 32 at the distal end of the arm 28. Adjustments made using the handle assembly 30 provide the optimal forces for achieving reduction and alignment of the distal fragment(s) 22 by providing combinations of palmar tilt and length restoration to the distal fragment(s) 22.

Figure 3B:
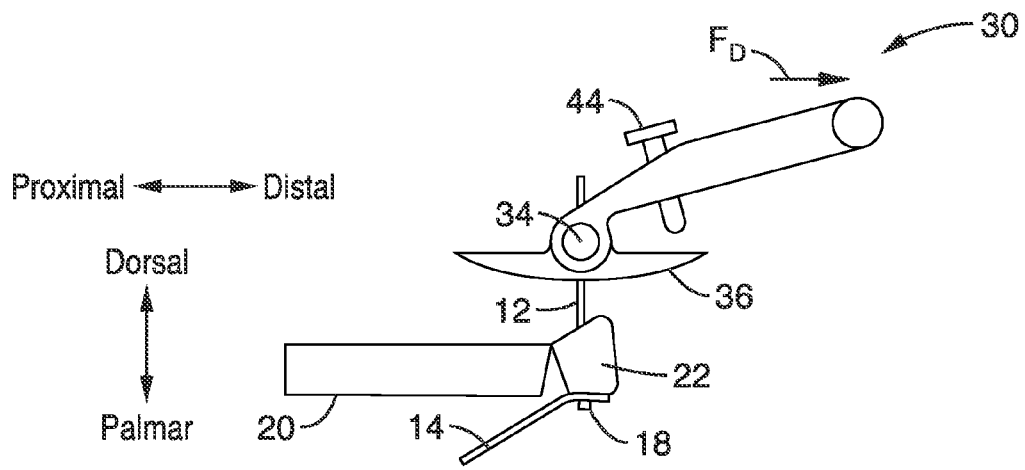

FIG. 3B shows an initial force $F_D$ applied by the surgeon's hand to the T-handle 32 in a distal direction. This force is transmitted through the pivot pin 12 to distract the distal fragments 22 and align the fracture in the proximal-distal direction.

Figure 3C:
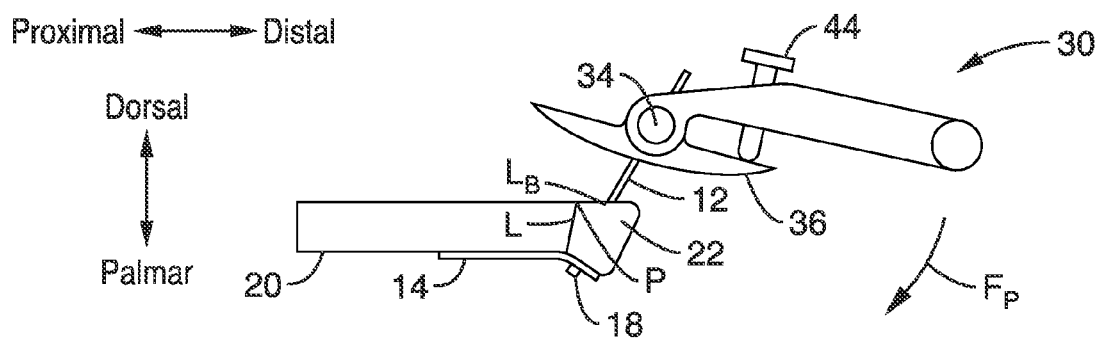

FIG. 3C shows a second force $F_P$ applied to the T-handle 32 that rotates $R_{HA}$ the T-handle 32 about the longitudinal axis $A_{PL}$ of the pivot link 34 in the palmar direction. As T-handle 32 rotates palmarwardly, the adjustment screw 44 contacts the dorsal platform 36, which is in contact with the dorsal surface of the patient's hand. Consequently, the second force $F_P$ applies a bending load $L_B$ to the pivot pin 12.

Because the dorsal surface of the distal fracture fragments 22 remain tethered by soft tissue to the radius 20 at the fracture line L, the bending load $L_B$ rotates the distal fragments 22 about a pivot point P at this soft tissue attachment location L. As a result of this rotational force, the palmar tilt is restored between the distal fragment(s) 22 and the radius 20. Additional translational or rotational forces may be applied by the surgeon to the T-handle 32 to achieve optimum alignment of the distal fracture fragments 22 with the distal end of the radius 20.

The combination of these force applications combined with the attachment location of the pivot pin 12 traversing through both the distal fracture fragment(s) 22 and the extensor retinaculum 24 enable the surgeon to: a) restore length to the radius, thereby realigning the distal radius to ulnar articular surfaces to optimize the articular mechanism for forearm rotation, b) create a torque on the distal fragment(s) that restores palmar tilt to the articular surface of the radius 20, and c) restore ulnar inclination to the distal radius articular surface.

Once the distal fracture fragment(s) 22 are aligned with the radius 20, and while the surgeon maintains this alignment by applying forces to the T-handle 32, the volar plate 14 is secured to the radius 20 with a plurality of screws and pegs through holes 52 and slot(s) 54 in the volar plate 14. Following attachment of the volar plate 14, the handle assembly 30 is removed from the pivot pin 12 and the pivot pin 12 is withdrawn from the distal fracture fragment(s) 22 (with bone drill, not shown).

FIG. 4 shows an alternative embodiment of a fracture reduction apparatus 70 in accordance with the present disclosure. Fracture reduction apparatus 70 uses two pivot pins, a radial pivot pin 72 and an ulnar pivot pin 74 (both of which may be identical in structure to pin 12 shown in FIG. 5). With the volar plate 14 positioned against the palmar surface of the radius 20, a pin bridge 43 is positioned against the palmar surface of the volar plate 14. The pin bridge 43 has two thru-holes, one on each of its radial and ulnar sides. Each pivot pin 72/74 is inserted through its thru-hole in the pin bridge 43 directly into the distal fracture fragment(s) 22 either radial or ulnar to the volar plate 14. A spherical stop 18 on each pivot pin 72, 74 prevents the pivot pins 72, 74 from passing through the thru-holes. The handle assembly 90 is attached to the exposed dorsal ends of the pivot pins 72, 74 by sliding the pivot pins 72, 74 through the two slots 78 in the dorsal platform 76 and two pin holes (not shown) in the pivot link 80. Pivot link 80 may be secured in the same way as link 34 shown in FIG. 1.

Once the dorsal platform 76 is positioned against the dorsal surface of the patient's distal forearm and wrist and the pivot pins 72, 74 are attached to the handle assembly 90, the pin bridge 43 abuts the volar plate 14 and holds it in the desired position against the distal end of the shaft of the radius 20. In this embodiment, the volar plate 14 is not constrained by a pivot pin 12 passing through a hole in the volar plate 14, as shown in FIG. 1. Consequently, the volar plate 14 can be repositioned without having to remove the pivot pins 74. By loosening the attachment of the dorsal ends of the pivot pins 72, 74 with the pivot link 80, the pin bridge 43 becomes loose against the volar plate 14, allowing the surgeon to reposition the volar plate 14 as required. The handle assembly 90 is then used as previously described in FIG. 3A to FIG. 3C above to align the distal fracture fragment(s) 22.

From the description herein, it will be appreciated that that the present disclosure encompasses multiple embodiments which include, but are not limited to, the following:

1. An apparatus for treating a fracture of the distal radius of a patient's hand, the apparatus comprising: a pivot pin configured to engage a patient's radius at an attachment point distal to the fracture of the radius; wherein the pivot pin has a sharpened end configured to pierce a palmar aspect of the radius and extend through the radius to at least a portion of an extensor retinaculum tissue associated with the radius; and a handle assembly configured to slidably engage the pivot pin at a dorsal location with respect to the patient's hand and attachment point; wherein the handle assembly is configured to fixedly engage the pivot pin such that manual manipulation of the handle assembly adjusts the position of the distal attachment point to realign the fracture of the distal radius.

2. An apparatus as in any of the previous embodiments: wherein the fractured radius comprises at least one distal bone fragment; wherein the distal attachment point is at a location at or adjacent to (and/or through) the at least one distal bone fragment; and wherein the handle assembly is configured to adjust the position of the distal bone fragment to realign the distal bone fragment with respect to the fracture of the distal radius.

3. An apparatus as in any of the previous embodiments, the handle assembly comprising: a dorsal platform comprising a surface configured to contact a dorsal surface associated with the radius; a handle; and a pivot link rotatably coupling the dorsal platform and the handle; wherein the handle is configured to rotate about a longitudinal axis of the pivot link with respect to the platform.

4. An apparatus as in any of the previous embodiments, wherein one or more of the dorsal platform and pivot link comprise an aperture to allow the handle assembly to slidably engage over the pivot pin.

5. An apparatus as in any of the previous embodiments, wherein the aperture in the dorsal platform is slotted to allow translational motion of the dorsal platform in proximal-distal direction with respect to the pivot pin to allow adjustment of the position of the at least one distal bone fragment in a proximal-distal direction with respect to the radius.

6. An apparatus as in any of the previous embodiments, wherein the pivot link comprises an aperture configured to allow slidable reciprocation of the pivot pin in a palmar-dorsal direction within the pivot link, the handle assembly further comprising: a locking member coupled to the pivot link; wherein the locking member is configured to fixedly engage the pivot pin to lock translation of the pivot pin with respect to the handle assembly.

7. An apparatus as in any of the previous embodiments, wherein the handle assembly is configured to adjust the position of the distal attachment point to adjust the position of the at least one distal bone fragment in one or more of: a palmar-dorsal direction with respect to the radius and a radial-ulnar direction with respect to the radius.

8. An apparatus as in any of the previous embodiments, wherein the handle assembly is configured to adjust the position of the distal attachment point to restore length to the fractured distal radius and realign the distal radius to ulnar articular surfaces.

9. An apparatus as recited in claim 4, wherein the handle assembly is configured to generate a torque on the at least one distal bone fragment to restore palmar tilt to an articular surface of the radius.

10. An apparatus as in any of the previous embodiments, wherein the handle assembly is configured to restore ulnar inclination to the distal radius articular surface by providing a torque to the at least one distal bone fragment such that it pivots about the distal end of the ulna.

11. An apparatus as in any of the previous embodiments: wherein the pivot pin comprises a palmar end and a dorsal end comprising the sharpened tip; and wherein the dorsal end of the pivot pin is configured to pass through the at least one distal bone fragment and the extensor retinaculum from a palmer surface of the radius to a dorsal surface of the radius.

12. An apparatus as in any of the previous embodiments: wherein the pivot pin is configured to pass through an aperture of a volar plate disposed on the palmer surface of the radius; wherein the pivot pin comprises a stop disposed toward the palmer end of the pivot pin; and wherein the stop is sized larger than the volar plate aperture to impede progress of the pivot pin in the dorsal direction past the stop and engage the volar plate.

13. A method for treating a fracture of the distal radius of a patient's hand, the method comprising: positioning a pivot pin at an attachment point distal to the fracture of the radius; the pivot pin comprising a sharpened end configured to engage a patient's radius; piercing a palmar aspect of the radius with the sharpened end and extending the pivot pin through the radius to at least a portion of an extensor retinaculum tissue associated with the radius;

slidably attaching a handle assembly to the pivot pin at a dorsal location with respect to the patient's hand and attachment point; fixedly engaging the pivot pin to the handle assembly; and applying manual manipulation of the handle assembly to adjust a position of the distal attachment point to realign the fracture of the distal radius.

14. A method as in any of the previous embodiments: wherein the fractured radius comprises at least one distal bone fragment; wherein the distal attachment point is at a location at or adjacent to the at least one distal bone fragment; and wherein adjusting a position of the distal attachment point comprises adjusting the position of the distal bone fragment to realign the distal bone fragment with respect to the fracture of the distal radius.

15. A method as in any of the previous embodiments, the handle assembly comprising: a dorsal platform comprising a surface configured to contact a dorsal surface associated with the radius; a handle; and a pivot link rotatably coupling the dorsal platform and the handle; wherein the handle is configured to rotate about a longitudinal axis of the pivot link with respect to the platform.

16. A method as in any of the previous embodiments, wherein one or more of the dorsal platform and pivot link comprise an aperture to allow the handle assembly to slidably engage over the pivot pin.

17. A method as in any of the previous embodiments, wherein the aperture in the dorsal platform is slotted to allow translational motion of the dorsal platform in proximal-distal direction with respect to the pivot pin to allow adjustment of the position of the at least one distal bone fragment in a proximal-distal direction with respect to the radius.

18. A method as in any of the previous embodiments, wherein the pivot link comprises an aperture configured to allow slidable reciprocation of the pivot pin in a palmar-dorsal direction within the pivot link, the handle assembly further comprising: a locking member coupled to the pivot link; wherein the locking member is configured to fixedly engage the pivot pin to lock translation of the pivot pin with respect to the handle assembly.

19. A method as in any of the previous embodiments, wherein adjusting the position of the distal attachment point comprises adjusting the position of the at least one distal bone fragment in one or more of: a palmar-dorsal direction with respect to the radius and a radial-ulnar direction with respect to the radius.

20. A method as in any of the previous embodiments, wherein adjusting the position of the distal attachment point comprises adjusting the position of the distal attachment point to restore length to the fractured distal radius and realign the distal radius to ulnar articular surfaces.

21. A method as in any of the previous embodiments, wherein adjusting the position of the distal attachment point comprises rotating the handle about the longitudinal axis of the pivot link to generate a torque on the at least one distal bone fragment to restore palmar tilt to an articular surface of the radius.

22. A method as in any of the previous embodiments, wherein adjusting the position of the distal attachment point comprises rotating the handle about the longitudinal axis of the pivot link to restore ulnar inclination to the distal radius articular surface by providing a torque to the at least one distal bone fragment such that it pivots about the distal end of the ulna.

23. A method as in any of the previous embodiments: wherein the pivot pin comprises a palmar end and a dorsal end comprising the sharpened tip; and wherein extending the pivot pin through the radius comprises passing the dorsal end of the pivot pin through the at least one distal bone fragment and the extensor retinaculum from a palmer surface of the radius to a dorsal surface of the radius.

24. A method as in any of the previous embodiments, wherein extending the pivot pin through the radius comprises: extending the pivot pin through an aperture of a volar plate disposed on the palmer surface of the radius; wherein the pivot pin comprises a stop disposed toward the palmer end of the pivot pin; and wherein the stop is sized larger than the volar plate aperture to impede progress of the pivot pin in the dorsal direction past the stop and engage the volar plate.

25. An apparatus for treating a fracture of the distal radius of a patient's hand, the apparatus comprising: a pivot pin configured to engage a patient's radius at an attachment point distal to the fracture of the radius; wherein the pivot pin has a sharpened end configured to pierce a palmar aspect of the radius and extend through the radius to at least a portion of an extensor retinaculum tissue associated with the radius; and a handle assembly comprising a dorsal platform having a surface configured to contact a dorsal surface associated with the radius, a handle and a pivot link rotatably coupling the dorsal platform and the handle; wherein one or more of the dorsal platform and pivot link comprise an aperture to allow the handle assembly to be slidably received over the pivot pin; and wherein the handle assembly is configured to fixedly engage the pivot pin a dorsal location with respect to the patient's hand and attachment point such that manual manipulation of the handle assembly adjusts the position of the distal attachment point to realign the fracture of the distal radius;

26. An apparatus as in any of the previous embodiments, wherein the handle is configured to rotate about a longitudinal axis of the pivot link with respect to the platform.

27. An apparatus as in any of the previous embodiments, wherein the aperture in the dorsal platform is slotted to allow translational motion of the dorsal platform in proximal-distal direction with respect to the pivot pin to allow adjustment of the position of the at least one distal bone fragment in a proximal-distal direction with respect to the radius.

28. An apparatus as in any of the previous embodiments: wherein the fractured radius comprises at least one distal bone fragment; wherein the distal attachment point is at a location at or adjacent to (and/or through) the at least one distal bone fragment; and wherein the handle assembly is configured to adjust the position of the distal bone fragment to realign the distal bone fragment with respect to the fracture of the distal radius.

29. An apparatus as in any of the previous embodiments, wherein the pivot link comprises an aperture configured to allow slidable reciprocation of the pivot pin in a palmar-dorsal direction within the pivot link, the handle assembly further comprising: a locking member coupled to the pivot link; wherein the locking member is configured to fixedly engage the pivot pin to lock translation of the pivot pin with respect to the handle assembly.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for treating a fracture of the distal radius of a patient's hand, the apparatus comprising:
   a pivot pin configured to engage a patient's radius at an attachment point distal to the fracture of the radius;
   wherein the pivot pin has a sharpened end configured to pierce a palmar aspect of the radius and extend through the radius to at least a portion of an extensor retinaculum tissue associated with the radius; and a handle assembly configured to slidably engage the pivot pin at a dorsal location with respect to the patient's hand and attachment point;

wherein the handle assembly is configured to fixedly engage the pivot pin such that manual manipulation of the handle assembly adjusts the position of the distal attachment point to realign the fracture of the distal radius;

wherein the fractured radius comprises at least one distal bone fragment;

wherein the distal attachment point is at a location at or adjacent to the at least one distal bone fragment; and wherein the handle assembly is configured to adjust the position of the distal bone fragment to realign the distal bone fragment with respect to the fracture of the distal radius, the handle assembly comprising:
- a dorsal platform comprising a surface configured to contact a dorsal surface associated with the radius;
- a handle;
- a pivot link rotatably coupling the dorsal platform and the handle;
- wherein the handle is configured to rotate about a longitudinal axis of the pivot link with respect to the platform;

wherein one or more of the dorsal platform and pivot link comprise an aperture to allow the handle assembly to slidably engage over the pivot pin;

wherein the pivot link comprises an aperture configured to allow slidable reciprocation of the pivot pin in a palmar-dorsal direction within the pivot link, the handle assembly further comprising:
- a locking member coupled to the pivot link; and
- wherein the locking member is configured to fixedly engage the pivot pin to lock translation of the pivot pin with respect to the handle assembly.

2. An apparatus as recited in claim 1, wherein the aperture in the dorsal platform is slotted to allow translational motion of the dorsal platform in proximal-distal direction with respect to the pivot pin to allow adjustment of the position of the at least one distal bone fragment in a proximal-distal direction with respect to the radius.

3. An apparatus as recited in claim 1, wherein the handle assembly is configured to adjust the position of the distal attachment point to adjust the position of the at least one distal bone fragment in one or more of: a palmar-dorsal direction with respect to the radius and a radial-ulnar direction with respect to the radius.

4. An apparatus as recited in claim 1, wherein the handle assembly is configured to adjust the position of the distal attachment point to restore length to the fractured distal radius and realign the distal radius to ulnar articular surfaces.

5. An apparatus as recited in claim 1, wherein the handle assembly is configured to generate a torque on the at least one distal bone fragment to restore palmar tilt to an articular surface of the radius.

6. An apparatus as recited in claim 1, wherein the handle assembly is configured to restore ulnar inclination to the distal radius articular surface by providing a torque to the at least one distal bone fragment such that it pivots about the distal end of the ulna.

7. An apparatus as recited in claim 1,
wherein the pivot pin comprises a palmar end and a dorsal end comprising the sharpened tip; and
wherein the dorsal end of the pivot pin is configured to pass through the at least one distal bone fragment and the extensor retinaculum from a palmer surface of the radius to a dorsal surface of the radius.

8. An apparatus as recited in claim 7:
wherein the pivot pin is configured to pass through an aperture of a volar plate disposed on the palmer surface of the radius;
wherein the pivot pin comprises a stop disposed toward the palmer end of the pivot pin; and
wherein the stop is sized larger than the volar plate aperture to impede progress of the pivot pin in the dorsal direction past the stop and engage the volar plate.

9. An apparatus for treating a fracture of the distal radius of a patient's hand, the apparatus comprising:
a pivot pin configured to engage a patient's radius at an attachment point distal to the fracture of the radius;
wherein the pivot pin has a sharpened end configured to pierce a palmar aspect of the radius and extend through the radius to at least a portion of an extensor retinaculum tissue associated with the radius; and
a handle assembly comprising a dorsal platform having a surface configured to contact a dorsal surface associated with the radius, a handle and a pivot link rotatably coupling the dorsal platform and the handle;
wherein one or more of the dorsal platform and pivot link comprise an aperture to allow the handle assembly to be slidably received over the pivot pin;
wherein the handle assembly is configured to fixedly engage the pivot pin at a dorsal location with respect to the patient's hand and attachment point such that manual manipulation of the handle assembly adjusts the position of the distal attachment point to realign the fracture of the distal radius;
wherein the pivot link comprises an aperture configured to allow slidable reciprocation of the pivot pin in a palmar-dorsal direction within the pivot link, the handle assembly further comprising:
a locking member coupled to the pivot link; and
wherein the locking member is configured to fixedly engage the pivot pin to lock translation of the pivot pin with respect to the handle assembly.

10. An apparatus as recited in claim 9, wherein the handle is configured to rotate about a longitudinal axis of the pivot link with respect to the platform.

11. An apparatus as recited in claim 10, wherein the aperture in the dorsal platform is slotted to allow translational motion of the dorsal platform in proximal-distal direction with respect to the pivot pin to allow adjustment of the position of the at least one distal bone fragment in a proximal-distal direction with respect to the radius.

12. An apparatus as recited in claim 9:
wherein the fractured radius comprises at least one distal bone fragment;
wherein the distal attachment point is at a location at or adjacent to the at least one distal bone fragment; and
wherein the handle assembly is configured to adjust the position of the distal bone fragment to realign the distal bone fragment with respect to the fracture of the distal radius.

* * * * *